(12) United States Patent
Ringström et al.

(10) Patent No.: US 9,138,497 B2
(45) Date of Patent: Sep. 22, 2015

(54) METHOD OF PRESTERILIZING AN ASEPTIC TANK AND CONNECTING CONDUITS

(75) Inventors: Roland Ringström, Veberöd (SE); Bo Olsson, Malmö (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 1053 days.

(21) Appl. No.: 12/522,103

(22) PCT Filed: Feb. 4, 2008

(86) PCT No.: PCT/SE2008/000091
§ 371 (c)(1),
(2), (4) Date: Jul. 2, 2009

(87) PCT Pub. No.: WO2008/100196
PCT Pub. Date: Aug. 21, 2008

(65) Prior Publication Data
US 2010/0111760 A1    May 6, 2010

(30) Foreign Application Priority Data

Feb. 12, 2007    (SE) ...................................... 0700323

(51) Int. Cl.
| | | |
|---|---|---|
| A61L 2/00 | (2006.01) | |
| B08B 9/00 | (2006.01) | |
| F16K 11/00 | (2006.01) | |
| A61L 2/04 | (2006.01) | |
| A23C 7/02 | (2006.01) | |
| A61L 2/07 | (2006.01) | |

(52) U.S. Cl.
CPC ... *A61L 2/04* (2013.01); *A23C 7/02* (2013.01); *A61L 2/07* (2013.01)

(58) Field of Classification Search
CPC .......... B08B 3/00; B08B 3/04; B08B 7/0064; A61L 2/00; A61L 2/18
USPC ............... 422/6, 38, 292, 295, 307; 134/22.1, 134/22.12; 137/238, 340–341
See application file for complete search history.

(56) References Cited

U.S. PATENT DOCUMENTS

| | | | | |
|---|---|---|---|---|
| 3,643,586 | A | * | 2/1972 | Robinson ........................ 53/510 |
| 4,156,741 | A | * | 5/1979 | Beauvais et al. ............... 426/131 |
| 4,583,453 | A | * | 4/1986 | Torterotot ........................ 99/455 |
| 5,527,516 | A | | 6/1996 | Yamamoto et al. |
| 5,759,491 | A | * | 6/1998 | Bunin ............................. 422/38 |

FOREIGN PATENT DOCUMENTS

| | | |
|---|---|---|
| DE | 31 51 609 A1 | 8/1982 |
| JP | 1 501 802 A | 2/1978 |
| JP | 2 052 949 A | 2/1981 |

OTHER PUBLICATIONS

International-Type Search Report mailed Jul. 25, 2007 in corresponding Swedish Application No. 0700323-9.
PCT/ISA/210 for PCT/SE2008/000091 completed Jun. 16, 2008.

\* cited by examiner

*Primary Examiner* — Monzer R Chorbaji
(74) *Attorney, Agent, or Firm* — Buchanan Ingersoll & Rooney PC

(57) ABSTRACT

A method of presterilizing an aseptic tank and connecting conduits involves pumping a certain amount of cold water into the tank and the conduits which is caused to pass through a heat exchanger. In the heat exchanger, the water is heated to 120-150° C., whereafter the water is pumped across the tank and conduits during 10-20 minutes.

18 Claims, 1 Drawing Sheet

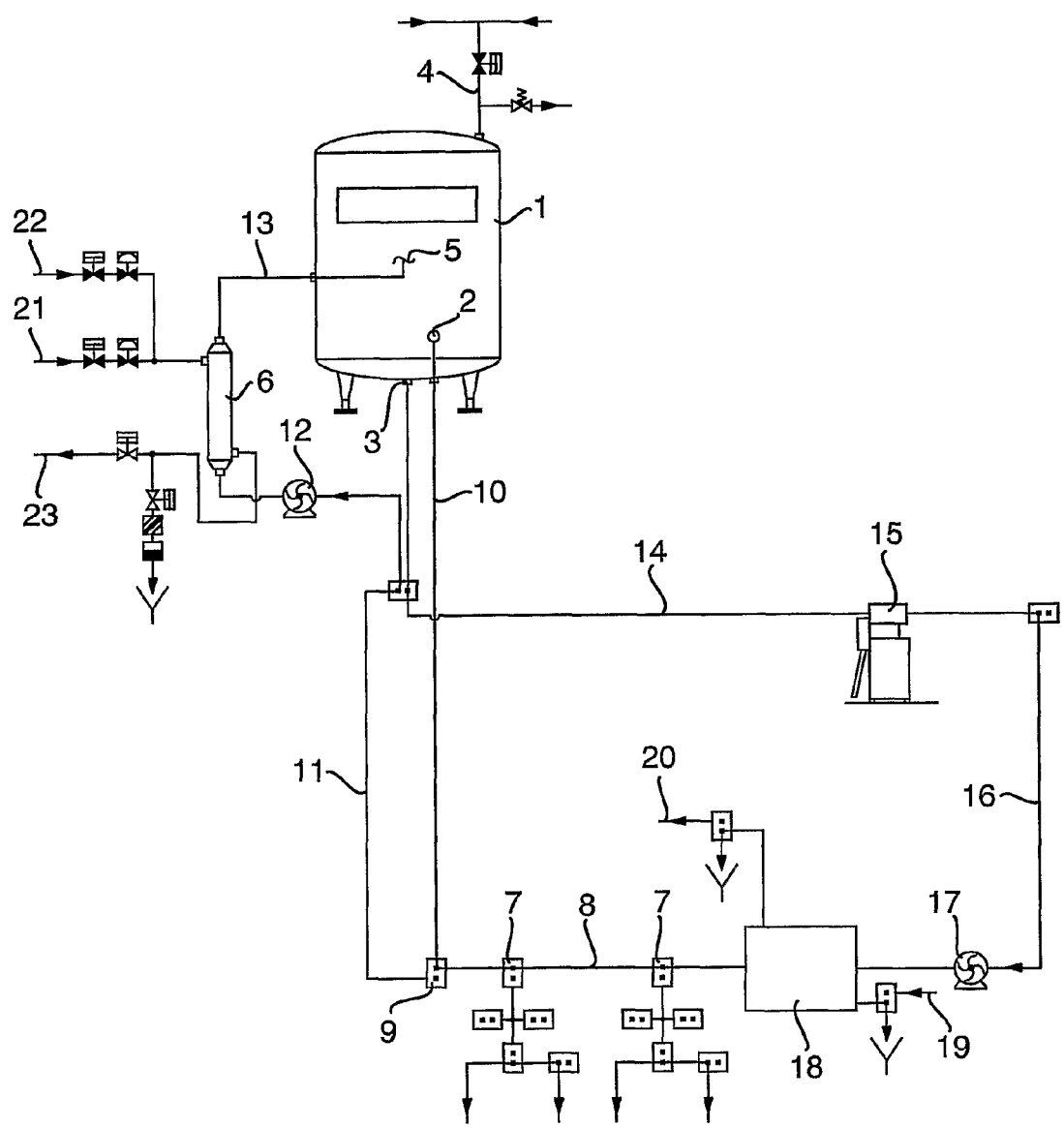

METHOD OF PRESTERILIZING AN ASEPTIC TANK AND CONNECTING CONDUITS

TECHNICAL FIELD

The present invention relates to a method of presterilizing an aseptic tank and connecting conduits.

BACKGROUND ART

Aseptic tanks or sterile tanks are employed within the food industry for temporarily storing a sterile product before it is filled, under aseptic conditions, into some form of aseptic package.

The product may, for example, be milk which has been heated to high temperature during a given predetermined time interval, so that it becomes sterile, so-called UHT treatment (Ultra High Temperature treatment). If the sterile product is packed in aseptic packages, it can thereafter be stored at room temperature for a lengthy period of time.

Aseptic tanks are needed as a buffer between the UHT plant and the filling machines which, for example, are to pack the sterile product into aseptic consumer packages. By employing sterile tanks, excess treatment or processing of the product is avoided when the capacity of the UHT plant does not always correspond to the capacity of the filling machine or machines. The aseptic tank can also be employed for temporary storage in operational disruptions.

Before the aseptic tank is made operational for production, it must, after washing, be presterilized. Today, steam is used to carry this presterilization into effect. Enormous amounts of steam are consumed at a temperature of approx. 130° C. and high pressure. In order reliably to evacuate all air from the tank and the connecting conduits, the steam injection is repeated several times, before the sterilization proper. The steam which is used for the presterilization cannot be recycled, but is ejected straight out into the atmosphere.

The method of presterilization using steam is not totally reliable, since air pockets in a tank and conduit can block the sterilization. Similarly, a certain condensation of steam takes place, above all in long conduits and valves, which lowers the temperature, with poorer sterilization as a result. After the presterilization with steam, both tank and conduits must be cooled down, and this is done using sterile water. A total presterilization with subsequent cooling takes roughly 1 hour and 10 minutes to carry out.

Problem Structure

One object of the present invention is to realise a method which affords a reliable presterilization of tank and conduits.

A further object of the present invention is to reduce the consumption of steam and to minimise the emission of steam into the atmosphere, which contributes to an improved working environment.

Yet a further object of the present invention is to realise a method which reduces the time used for the presterilization.

Still a further object of the present invention is to reduce the consumption of energy and effects on the environment by optimising the consumption of water for carrying the method into effect.

Solution

These and other objects have been attained according to the present invention in that the method of the type described by way of introduction has been given the characterising features that a given quantity of cold water is pumped into said tank and said conduits, that the water is caused to pass a heat exchanger, in which the water is heated to 120-150° C., whereafter the water is pumped under pressure through the tank and conduits during 10-20 minutes.

Preferred embodiments of the present invention have further been given the characterising features as set forth in the appended subclaims.

BRIEF DESCRIPTION OF THE ACCOMPANYING DRAWING

One preferred embodiment of the present invention will now be described in greater detail hereinbelow, with reference to the accompanying Drawing, in which:

FIG. 1 schematically illustrates a flow diagram for carrying the method according to the invention into effect.

DESCRIPTION OF PREFERRED EMBODIMENT

The flow diagram includes at least one aseptic tank 1 or sterile tank. The aseptic tank has an inlet 2 for product, positioned preferably in the lower region of the tank 1. The aseptic tank 1 further displays an outlet 3 positioned in the lowest region of the tank 1. The aseptic tank normally also displays a sterile filter positioned in the upper region of the tank 1. In FIG. 1, the sterile filter is illustrated as a connection 4. For carrying the method into effect, the aseptic tank 1 is also provided with a nozzle 5 positioned centrally in the tank 1.

The plant for carrying the method into effect also includes a heat exchanger 6. In the preferred embodiment, the heat exchanger 6 consists of a tube heat exchanger, but other types of heat exchangers, for example plate heat exchangers, may be used.

The aseptic tank 1 is intended to be used for the intermediate storage of ready-treated product before filling of the product into aseptic packaging containers. The aseptic tank 1 is most generally necessary, since the capacity of the equipment treating the product not always corresponds with the filling capacity of the plant. The aseptic tank 1 may also constitute a buffer in the event of operational disruptions.

The ready-treated product arrives from one or more heat treatment units (not shown) by the intermediary of valves 7 into the conduit 8. The conduit 8 is connected to a valve 9. From the valve 9, a conduit 10 leads to the product inlet 2 of the aseptic tank 1. It is via this conduit that the ready-treated product enters into the tank 1.

A conduit 11 also leaves the valve 9 and, via a centrifugal pump 12, or corresponding pump, leads to the heat exchanger 6. From the heat exchanger 6, a conduit 13 leads further to the nozzle 5, positioned in the tank 1.

The conduits 11 and 13 are connected to the one flow side of the heat exchanger 6. An inlet 21 for steam is connected to the other flow side of the heat exchanger 6, and the same inlet may also be utilised as an inlet 22 for cooling water. From the other flow side, there is an outlet 23 for condensed steam and heated cooling water, respectively.

From the outlet 3 of the aseptic tank 1, there is disposed a conduit 14 which leads to one or more filling machines 15 for aseptic filling of the product in aseptic packages. The packages may, for example, be aseptic consumer packages of single-use disposal type.

Through a valve arrangement (not shown), the conduit 14 may be connected directly to the filling machine 15. Alternatively, the conduit 14 may, through the valve arrangement, be connected to the conduit 16 which, via a centrifugal pump 17, or corresponding pump, leads to a valve battery 18.

The valve battery 18 is also connected to the conduit 8. The valve battery 18 has an inlet 19 which may be connected to a washing unit (not shown), where detergents and water may be taken in, as well as an outlet 20 for spent detergent and water which has been circulated through the plant. Cleaning of the plant may take place without this needing to be dismantled, so-called CIP (Cleaning In Place).

After washing of the plant, the aseptic tank 1 and the surrounding conduits 8, 10, 14 must be presterilized before the tank 1 can be used to store ready-treated, sterile product.

The method according to the present invention entails that cold water is pumped into the conduits 8, 10, 11, 13, 14, 16 and into the aseptic tank 1, so that the conduits 8, 10, 11, 13, 14, 16 are filled with water and the tank 1 only contains a slight amount of water. The amount of water corresponds to approximately 1-10% of the total volume of the tank 1, preferably 1-5% of the total volume. Cold water may suitably be pumped into the plant via the valve battery 18.

Before the presterilization, air at atmospheric pressure is enclosed in the tank 1. No other air or gas is supplied to the tank 1 during the presterilization. The conduit 4 from the sterile filter is kept closed during the presterilization in order to protect the sterile filter. The sterile filter is sterilized separately using steam.

The water is pumped around in the conduits 8, 11, 14, 16 while being heated by means of steam in the heat exchanger 6. The water is heated to 120-150° C., preferably to 130-150° C., in that the pressure is simultaneously built up, on the one hand across the tank 1, and on the other hand across the surrounding conduits 8, 10, 11, 14, 16. The pressure in the system is approx. 3 bar when the presterilization takes place.

Steam is fed to the heat exchanger 6 through the inlet 21. That steam which is used for heating may be recycled to the boiler in a closed circuit, which reduces the total energy resources required in the presterilization.

Hot water will be sprayed on the inside of the aseptic tank 1 by means of the nozzle 5. The nozzle 5 has a high flow capacity and it rotates in all directions, so that it spreads the hot water to all parts of the tank 1. The nozzle 5 may advantageously, during intermediate storage of product, be employed as piping for special products which may sediment or settle, such as flavoured milk and juices containing fibres.

The heated water is pumped around for approx. 10-20 minutes, preferably 10-15 minutes, which gives a reduced time for presterilization of tank 1 and conduits 8, 10, 11, 13, 14, 16. During the presterilization, the valve 9 is alternatingly switched so that the conduit 10 will also be sterilized.

By presterilizing with hot water, no air pockets occur in the tank 1 or the conduits 8, 10, 11, 13, 14, 16 where equipment would run the risk of not becoming sterilized. This method also avoids the condensation which may occur in presterilization with steam, where the condensation would give a lower temperature with consequential poorer sterilization result. In condensation pockets in conduits and valves or in long conduits, the temperature may be 10-20° C. lower than the temperature of the steam.

Once the presterilization is completed, the same water which was used for sterilization may be employed for cooling down the equipment. By connecting in cold water to the heat exchanger 6 through the inlet 22, the water which is circulated across the tank 1 and the conduits 8, 10, 11, 13, 14, 16 is cooled in the same manner as the hot water is circulated during the presterilization. The water is thereafter run to discharge via the valve battery 18.

If steam is employed for presterilization, use is often made of a cooling jacket to cool the tank 1. Since there is then no air remaining in the tank 1, air must be supplied via the sterile filter. The sterile filter must be dimensioned correspondingly, which would then entail larger sterile filters. In presterilization using hot water, there are both air and water in the tank 1. This implies that the cooling is considerably more rapid and a smaller volume of sterile air needs to be supplied.

The total presterilization time comprising heating, presterilization and cooling has proved in trials to amount to approx. 50 minutes, which is a reduction by 20 minutes compared with the total time involved in presterilization using steam. As a result, a closer approximation has been made to that time it takes to presterilize a filling machine, which today amounts to approx. 45 minutes. As a result, the availability of the equipment has been increased and this makes for longer production time.

Presterilization with hot water contributes in improving the working environment in the premises where the plant is located, since no steam is released in the premises. Previously employed methods, using steam sterilization, have entailed that large quantities of steam have been released into the atmosphere, i.e. in the production premises. Presterilization using hot water also gives a more uniform temperature across the tank 1 and the connecting conduits 8, 10, 11, 13, 14, 16. There is less of a difference between the highest and the lowest temperature in the equipment. In the prior art presterilization using steam, it has been necessary to overcompensate in order that the lowest temperature will not be too low.

The plant for carrying the method according to the present invention into effect may also be employed when the intention is to carry out sterile intermediate washing in the event of product change. Sterile water may then be taken from the heat treatment equipment (not shown) and this water is heated in the existing heat exchanger 6 and circulated across the aseptic tank 1 and connecting conduits 8, 10, 11, 13, 14, 16. Sterile intermediate washing is not possible to carry out if the tank 1 is presterilized with steam.

As will have been apparent from the foregoing description, the present invention realises a method for presterilizing an aseptic tank and connecting conduits, which is safe and reliable. The method reduces the time for carrying out the presterilization and also contributes in achieving an improved working environment in the production premises. The consumption of energy and effects on the environment are also reduced in that it is possible using this method to optimise the consumption of water.

What is claimed is:

1. A method of presterilizing an aseptic tank configured to store a ready-treated sterile liquid food product and connecting conduits configured to convey the ready-treated sterile liquid food product wherein a certain quantity of cold water is initially pumped into said tank and said conduits; and that the cold water is caused to pass through a heat exchanger in which the cold water is heated to 120-150° C. to simultaneously increase pressure in the aseptic tank and the connecting conduits, whereafter the water heated to 120-150° C. is pumped under pressure across the tank and the conduits so that the aseptic tank is presterilized to receive and store the ready-treated sterile liquid food product and so that the conduits are presterilized to convey the ready-treated sterile liquid food product into the presterilized aseptic tank.

2. The method as claimed in claim 1, wherein the water is pumped across the tank and the conduits during 10-15 minutes.

3. The method as claimed in claim 1, wherein the water is heated in the heat exchanger to 130-150° C.

4. The method as claimed in claim 1, wherein the amount of water which is pumped into the aseptic tank and the conduits constitutes approx. 1-10% of the total volume of the aseptic tank.

5. The method as claimed in claim 1, wherein the amount of water which is pumped into the aseptic tank and the conduits constitutes approx. 1-5% of the total volume of the aseptic tank.

6. The method as claimed in claim 1, wherein the heat exchanger consists of a tube heat exchanger.

7. The method as claimed in claim 1, wherein the heated water is distributed inside the aseptic tank by means of a nozzle.

8. The method as claimed in claim 1, wherein the water which has been used for presterilization is thereafter cooled in the heat exchanger and used to cool down the aseptic tank and the connecting conduits.

9. The method as claimed in claim 1, wherein the water heated to 120-150° C. is pumped under pressure across the tank and the conduits for 10-20 minutes.

10. A method of presterilizing an aseptic tank to which is connected connecting conduits, the aseptic tank being configured to store a ready-treated sterile liquid food product and the connecting conduits being configured to convey the ready-treated sterile liquid food product, the method comprising:
    enclosing air at atmospheric pressure in the tank;
    initiating presterilization by initially pumping cold water into the tank so that the cold water flows into the tank and also along at least some of the connecting conduits;
    heating the cold water flowing through the connecting conduits by way of a heat exchanger to heat the cold water to 120° C.-150° C. and simultaneously increase pressure in the aseptic tank and connecting conduits;
    pumping the water heated to 120° C.-150° C. so that the conduits are presterilized to convey the ready-treated sterile liquid food product and so that the aseptic tank is presterilized to receive and store the ready-treated sterile liquid food product conveyed by the conduits; and
    wherein no gas or air is supplied to the tank during the presterilization.

11. The method as claimed in claim 10, wherein the heat exchanger includes an inlet for introducing the cold water into the heat exchanger, the cold water being heated by way of steam in the heat exchanger.

12. The method as claimed in claim 10, wherein an amount of water pumped into the tank and the conduits is approximately 1-10% of a total volume of the tank.

13. The method as claimed in claim 10, wherein the heat exchanger is a tube heat exchanger.

14. The method as claimed in claim 10, further comprising distributing the heated water inside the tank by a nozzle.

15. The method as claimed in claim 10, further comprising cooling the heated water in the heat exchanger after the time period, and pumping the cooled water through the connecting conduits and the tank to cool the tank and the connecting conduits.

16. The method as claimed in claim 10, wherein the pumping of the water heated to 120° C.-150° C. comprises pumping the water heated to 120° C.-150° C. for a time period of 10-20 minutes.

17. A method of presterilizing an aseptic tank and conduits connected to the aseptic tank, the aseptic tank being configured to store a ready-treated sterile liquid food product before being packaged in aseptic packages and the connecting conduits being configured to convey the ready-treated sterile liquid food product into and out of the aseptic tank before being packaged, the method comprising:
    initiating presterilization by initially pumping cold water into the tank so that the cold water flows into the tank and also along at least some of the connecting conduits;
    heating the cold water flowing through the connecting conduits by way of a heat exchanger to heat the cold water to 120° C.-150° C. and simultaneously increase pressure in the aseptic tank and connecting conduits;
    pumping the water heated to 120° C.-150° C. so that the conduits are presterilized conduits and the aseptic tank is a presterilized aseptic tank into which the ready-treated sterile liquid food product is introduced by way of the presterilized conduits and stored for later packaging in the aseptic packages;
    the pumping of the cold water, the heating of the cold water, and the pumping of the water heated to 120° C.-150° C. taking place before the ready-treated sterile liquid food product is conveyed along the conduits and before the ready-treated sterile liquid food product is introduced into the tank; and
    the water being maintained in a liquid state during the presterilization of the aseptic tank and the conduits.

18. The method as claimed in claim 17, wherein the pumping of the water heated to 120° C.-150° C. comprises pumping the water heated to 120° C.-150° C. for a time period of 10-20 minutes.

* * * * *